United States Patent [19]

Tarr

[11] Patent Number: 5,085,663
[45] Date of Patent: Feb. 4, 1992

[54] SURGICAL KNIFE WITH ANGULAR CUT CONTROL AND METHOD OF USING THE SAME

[76] Inventor: Bernard Tarr, 1688 Meridian Ave., Miami Beach, Fla. 33139

[21] Appl. No.: 724,468

[22] Filed: Jun. 27, 1991

Related U.S. Application Data

[63] Continuation of Ser. No. 457,950, Dec. 27, 1989, abandoned.

[51] Int. Cl.⁵ .............................................. A61B 17/32
[52] U.S. Cl. ................................... 606/172; 30/294
[58] Field of Search ................ 606/167, 166, 172; 30/294, 286, 289, 293, 317, 290

[56] References Cited

U.S. PATENT DOCUMENTS

| 601,315 | 3/1898 | Creveling | 30/294 |
|---|---|---|---|
| 1,946,731 | 2/1934 | Castain | 30/294 |
| 2,932,296 | 4/1960 | Sanders | 606/167 |
| 3,889,368 | 6/1975 | Himeno . | |
| 3,905,101 | 9/1975 | Shepherd . | |
| 3,945,117 | 3/1976 | Beaver . | |
| 4,062,116 | 12/1977 | Arnott . | |
| 4,114,624 | 9/1978 | Haverstock | 606/167 |
| 4,324,044 | 4/1982 | Shahinian, Jr. . | |
| 4,373,263 | 2/1983 | Ayers | 30/294 |
| 4,473,076 | 9/1984 | Williams et al. . | |

FOREIGN PATENT DOCUMENTS 2179859  3/1987  United Kingdom ................ 606/166

OTHER PUBLICATIONS

Principals of Surgical Technique, The Art of Surgery, Second Ed., Gary G. Wind/Normal M. Rich, Urban and Schwarzenberg, Baltimore-Munich, 1987, pp. 66 & 67.

Primary Examiner—Michael H. Thaler
Attorney, Agent, or Firm—Larson & Taylor

[57] ABSTRACT

A surgical knife is provided with angular cut control comprising rollers which extend along each side of the knife edge to maintain the knife blade in perpendicular relationship with respect to the surface being cut. The rollers additionally perform the function of smoothing out the surface to be cut and provide directional stability during the formation of the surgical incision.

5 Claims, 1 Drawing Sheet

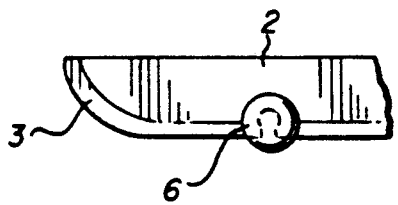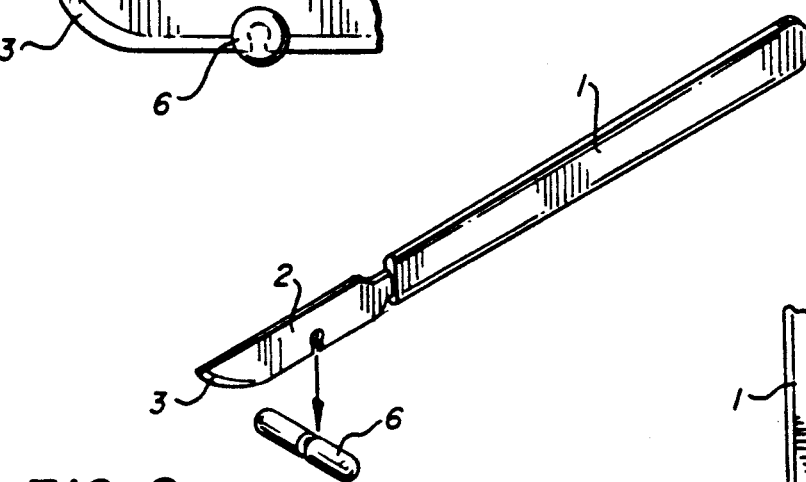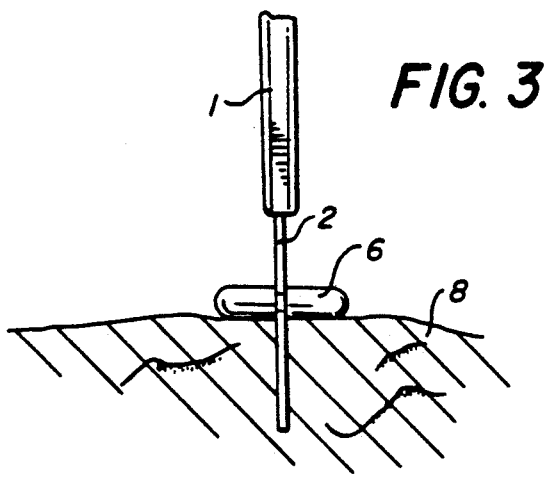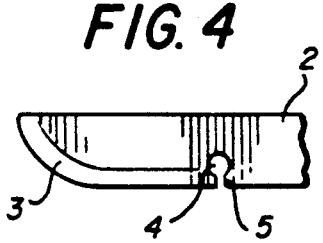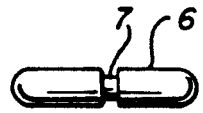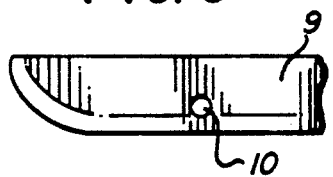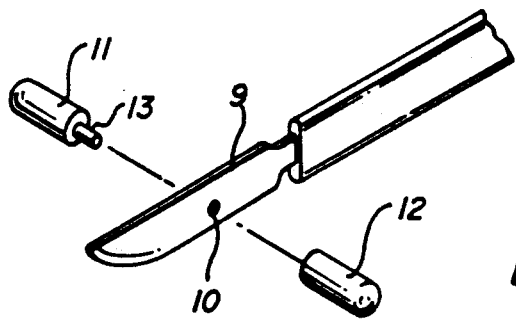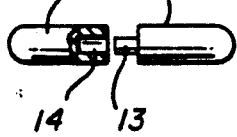

SURGICAL KNIFE WITH ANGULAR CUT CONTROL AND METHOD OF USING THE SAME

This application is a continuation of application Ser. No. 457,950 filed Dec. 27, 1989, now abandoned.

BACKGROUND OF THE INVENTION

The present invention relates to a surgical knife which is provided with means for maintaining the cutting edge of the knife blade in perpendicular relationship with respect to the surface being cut and which provides for directional stability during the cutting operation.

It is well known in the prior art to provide surgical knives in which the depth of the cut into the skin is controlled. For example, the Shahinian U.S. Pat. No. 4,324,044 discloses a knife which is provided with a guard surface which is maintained substantially parallel to the surface to be cut. The guard surface thus limits the initial depth of the cut by preventing the handle of the knife from following the blade into the incision. Similarly, the Beaver U.S. Pat. No. 3,945,117 discloses a surgical knife having a guard which frictionally grips the blade so that the guard may be adjusted on the blade. The guard limits the depth of the cut which may be made into the skin. The Williams U.S. Pat. No. 4,473,076 also provides a surgical knife which permits accurate control of incision depth and further provides for improved visibility of the incision being made. However, there is no teaching in the prior art of a surgical knife in which the knife blade is maintained in a plane which is perpendicular to the skin surface by means of a pair of rollers which smooth the surface of the skin and retain the incision line in vertical orientation with respect to the surface of the skin. The Arnott U.S. Pat. No. 4,062,116 discloses a fabric cutting tool which has a central blade with a pair of guide wheels which assist in moving the cutting tool along a piece of fabric.

According to the present invention, there is provided a scalpel having a roller on each side of the blade at a point spaced rearwardly of the blade tip. The rollers are supported on a shaft which passes through an aperture in the knife blade. The radius of the roller is slightly greater than the distance from the center of the hole in the blade to the knife edge. Thus, the rollers extend beyond the knife edge and roll along the skin surface as the incision is being made. The rollers serve the function of maintaining the knife blade in a perpendicular plane with respect to the skin surface and the rollers further perform the function of smoothing out the skin surface immediately adjacent the cutting edge of the knife blade. The depth of the incision may be controlled by the inclination of the scalpel with respect to the skin, that is, by moving the handle of the surgical knife up or down with respect to the skin surface. The advantage in maintaining the knife blade at a 90° angle with respect to the surface of the skin is to enable the surgeon to maintain directional stability during the formation of the incision so as to provide a more perfect closure. A surgical incision made at a right angle with respect to the skin facilitates subsequent skin closure with the skin edges anatomically coapted in a more precise fashion. More precise skin closure results in primary intention healing with improved scar cosmesis and lessens wound healing complications such as infection and secondary intention healing.

An object of the present invention is to provide a surgical knife with means for retaining the knife blade in a plane perpendicular to the surface of the skin.

Another object of the present invention is to provide a scalpel with a pair of rollers which perform the dual function of maintaining the knife blade in perpendicular relationship to the skin surface and also maintains the skin surface in a smooth even plane as it is being cut.

Other objects and many of the attendant advantages of the present invention will become more readily apparent upon consideration of the following detailed specification in connection with the accompanying drawing wherein:

DETAILED DESCRIPTION OF THE DRAWINGS

FIG. 1 is a partial side elevation of a portion of the knife blade of a scalpel, FIG. 2 is an exploded perspective view showing a scalpel with the rollers in detached relationship, FIG. 3 is an end elevation showing a scalpel in accordance with the present invention forming an incision in the skin surface, FIG. 4 is a side elevation of the knife blade similar to FIG. 1 with the rollers removed, FIG. 5 is an elevational view of the rollers shown in the FIG. 1 to 3 embodiment, FIG. 6 is a side elevational view of a portion of a knife blade illustrating another embodiment of the invention, FIG. 7 is an elevational view partially in section showing the rollers used with the FIG. 6 knife blade, and FIG. 8 is a perspective view with the rollers shown removed from the knife blade.

DETAILED DESCRIPTION OF THE PREFERRED EMBODIMENT

There is shown in FIG. 2 a scalpel including a handle portion 1 and a blade portion 2. The blade is provided with a cutting edge 3 which extends from the tip of the blade and is curved as shown in FIG. 1 around the lower surface of the blade. It can be seen in FIG. 4 that the blade 2 is provided with an aperture 4 which is disposed adjacent the lower surface of the knife blade 2 adjacent the end portion of the cutting edge 3. There is a slot 5 which interconnects the lower edge of the blade 2 with the aperture 4. A roller 6 is provided with a central cutout portion to form a reduced shaft 7. Shaft 7 is of a diameter such that the shaft may be forced through passageway 5 and snapped into aperture 4 so that roller 6 rotates smoothly within the aperture in knife blade 2. As shown in FIG. 1, the periphery of the roller 6 extends slightly beyond the lower edge of the knife blade 2. Thus, when the surgeon is making an incision in skin 8 as shown in FIG. 3, the roller 6 performs the function of both maintaining the knife blade 2 at right angles with respect to the surface of the skin 8 and also smoothes the skin surface as the incision is being formed.

In one embodiment of the invention the center of the rollers are located approximately one-half inch rearwardly of the blade tip and each roller has a length of approximately one-half inch. In order to maintain directional stability, each roller should be at least one-half inch although longer rollers may be used. It is also within the scope of the invention to utilize gripping means on the roller surface such as projections or indentations to provide a tread like surface.

In FIGS. 6 to 8 another embodiment of the present invention is performed wherein it can be seen that a knife blade 9 is provided with an aperture 10 to receive a pair of separable rollers 11 and 12. As seen in FIG. 7, the roller 11 has a shaft 13 of reduced diameter extending from one end thereof. Roller 12 has a recess 14 in one end thereof which forms a tight pressed fit with the shaft 13. Rollers 11 and 12 are assembled on the knife blade 9 by inserting the shaft 13 within aperture 10 and press fitting the roller 12 on the end portion of shaft 13 so that the rollers 11 and 12 may rotate freely on the knife blade 9.

It can be seen that the knife blade of the surgeon's cutting instrument is maintained at a 90° angle with respect to the skin surface by virtue of the present invention. The rollers disposed on both sides of the knife blade permit the knife to be maintained at this perpendicular relationship to the skin surface while the skin to be cut is maintained as a smooth surface during the cutting operation.

Obviously many modifications and variations of the present invention are possible in light of the above teachings.

What is claimed as new and desired to be secured by Letters Patent is:

1. A surgical knife having a handle portion and blade portion extending along a single longitudinal axis, the blade having side faces and upper and lower edges with a cutting edge extending from one end of the upper edge of the blade and curving around the end portion of the blade and along the lower edge portion of the blade and terminating intermediate the length of the lower edge portion of the blade, roller means mounted in a nonadjustable fixed position on the blade along the lower edge portion of the blade whereby substantially all of the cutting edge of the knife is disposed between the roller means and said end portion of the upper edge of the blade, said roller means extending on both sides of the blade laterally with resect to the plane of the blade, the roller means on each side of the blade being of sufficient length to maintain directional stability of the blade when in use whereby when said roller means engages the skin to be cut said roller means smoothes the skin surface, maintains the cutting edge of the blade at a right angle with respect to the skin surface being cut and provides a pivot point on the skin surface so that the depth of the cut in the skin surface may be adjusted by raising or lowering the handle portion of the knife.

2. A surgical knife according to claim 1 wherein said roller means includes a single roller having a reduced central shaft portion and an aperture in said blade with a slot interconnecting an edge portion of the blade with the aperture so that the reduced shaft portion may be pressed through the slot into the aperture in the blade.

3. A surgical knife according to claim 1 wherein said roller means includes a pair of rollers, one of said rollers having a shaft of reduced diameter on one end thereof and the other of said rollers having a recess to receive the shaft with a press fit and an aperture in said blade to receive the shaft whereby the rollers rotate freely on the blade.

4. A surgical knife according to claim 1 wherien said roller means extends laterally on each side of the blade at least one half inch.

5. A method of forming an incision in the surface of skin with a scalpel having a handle portion and a blade portion extending on a longitudinal axis with the blade portion comprising a curved knife edge extending from the distal end and along the lower edge of the scalpel and roller means mounted in a nonadjustable fixed position on the blade and extending outwardly at right angles with respect to the side faces of the scalpel, said roller means being disposed intermediate the handle portion and blade portion along the lower edge of the scalpel, comprising the steps of inserting the blade tip into the skin until the skin surface contacts the roller means, inclining the scalpel about the roller means at an acute angle with respect to the skin surface to determine the depth of the cut of the scalpel in the skin, and moving the scalpel across the skin with the roller means smoothing the skin surface and maintaining the scalpel blade at a 90° angle with respect to the skin surface.

* * * * *